United States Patent
Barth et al.

(10) Patent No.: US 7,994,366 B2
(45) Date of Patent: Aug. 9, 2011

(54) PROCESS FOR CONTINUOUSLY PREPARING METHYL MERCAPTAN FROM CARBON- AND HYDROGEN-CONTAINING COMPOUNDS

(75) Inventors: Jan-Olaf Barth, Frankfurt (DE); Hubert Redlingshoefer, Muenchsteinach (DE); Caspar-Heinrich Finkeldei, Alzenau (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 516 days.

(21) Appl. No.: 12/126,322

(22) Filed: May 23, 2008

(65) Prior Publication Data

US 2008/0293974 A1    Nov. 27, 2008

(30) Foreign Application Priority Data

May 25, 2007   (DE) .................... 10 2007 024 576

(51) Int. Cl.
*C07C 321/00*   (2006.01)
(52) U.S. Cl. .......... 568/70; 518/705; 518/714; 518/718; 502/335
(58) Field of Classification Search .................. None
See application file for complete search history.

(56) References Cited

U.S. PATENT DOCUMENTS

| | | | |
|---|---|---|---|
| 4,410,731 A | 10/1983 | Buchholz | 568/70 |
| 4,570,020 A | 2/1986 | Ratcliffe et al. | 568/70 |
| 4,665,242 A | 5/1987 | Boulinguiez et al. | 568/70 |
| 4,668,825 A | 5/1987 | Ratcliffe et al. | 568/70 |
| 5,866,721 A | 2/1999 | Hofen et al. | 568/71 |

FOREIGN PATENT DOCUMENTS

| | | |
|---|---|---|
| DE | 1 768 826 | 8/1971 |
| EP | 0 850 923 | 7/1998 |
| GB | 1 268 842 | 3/1972 |
| WO | WO 00/56692 | 9/2000 |
| WO | WO 01/96290 | 12/2001 |
| WO | WO 2005/021491 | 3/2005 |
| WO | WO 2005/040082 | 5/2005 |
| WO | WO 2006/015668 | 2/2006 |
| WO | WO 2006/063669 | 6/2006 |

OTHER PUBLICATIONS

Barrault et al., {Synthesis of methyl mercaptan from carbon oxides and H2S with tungsten—alumina catalysts, Applied Catalysis, vol. 33, Issue 2, Sep. 15, 1987, pp. 309-330}.

*Primary Examiner* — Jafar Parsa
*Assistant Examiner* — Yate K Cutliff
(74) *Attorney, Agent, or Firm* — Oblon, Spivak, McClelland, Maier & Neustadt, L.L.P.

(57) ABSTRACT

Provided is a process for continuously preparing methyl mercaptan by reacting a reactant mixture comprising solid, liquid and/or gaseous carbon- and/or hydrogen-containing compounds with air or oxygen, and/or water and sulfur.

41 Claims, 1 Drawing Sheet

PROCESS FOR CONTINUOUSLY PREPARING METHYL MERCAPTAN FROM CARBON- AND HYDROGEN-CONTAINING COMPOUNDS

CROSS-REFERENCE TO RELATED APPLICATIONS

The present application claims priority to German patent application DE 102007024576.0, filed on May 25, 2007. German patent application DE 102007024576.0 is hereby incorporated by reference in its entirety.

BACKGROUND OF THE INVENTION

1. Field of the Invention

The present invention relates to a process for continuously preparing methyl mercaptan by reacting a reactant mixture comprising solid, liquid and/or gaseous carbon- and/or hydrogen-containing compounds with air or oxygen, and/or water and sulfur.

2. Discussion of the Background

Methyl mercaptan (a.k.a., methanethiol) is an industrially important intermediate for the synthesis of methionine and for the preparation of dimethyl sulfoxide and dimethyl sulfone.

Various conventional processes have been described for preparing methyl mercaptan. Methyl mercaptan is predominantly prepared by a methanol based process, whereby methanol and hydrogen sulfide are reacted over a catalyst consisting of an aluminum oxide support, transition metal oxides, and basic promoters. Methyl mercaptan is usually synthesized in the gas phase at temperatures between 300° C. and 500° C. and at pressures between 1 bar and 25 bar. The gas product mixture comprises the methyl mercaptan thus formed, water, unconverted methanol and hydrogen sulfide starting materials, dimethyl sulfide and dimethyl ether byproducts, and small amounts of polysulfides, such as dimethyl disulfide. Gases which are inert in the context of the reaction, for example carbon monoxide, carbon dioxide, nitrogen and hydrogen, are also present in the gas product mixture. The methyl mercaptan thus formed is removed from the gas product mixture in a plurality of distillation and wash columns operating at temperatures between 10° C. and 140° C., as described in U.S. Pat. No. 5,866,721.

Methyl mercaptan may alternatively be prepared from carbon oxides, hydrogen, sulfur and/or hydrogen sulfide. For example, methyl mercaptan may be prepared over catalysts based on alkali metal tungstates, as described in U.S. Pat. No. 4,665,242. In addition, U.S. Pat. No. 4,410,731 describes a process for preparing methyl mercaptan from carbon oxides, hydrogen, hydrogen sulfide or sulfur, and catalysts based on alkali metal molybdenum sulfides comprising transition metal oxides as promoters and aluminum oxide as a support. Furthermore, WO 2005/040082 describes a process for preparing methyl mercaptan from carbon oxides, hydrogen, hydrogen sulfide or sulfur, and catalysts based on alkali metal molybdates comprising transition metal oxides as promoters and silicon dioxide as a support. However, these processes have lower selectivities for methyl mercaptan and lower conversions of carbon oxides, as compared to the methanol based process.

An additional alternative to the methanol based process includes preparing methyl mercaptan from hydrogen and carbon disulfide or carbonyl sulfide. However, this alternative process is characterized by comparatively low selectivities for methyl mercaptan, a multitude of byproducts that are difficult and costly to remove, and the necessity of handling large amounts of byproducts including toxic carbon disulfide or carbonyl sulfide.

A commonality amongst the above-mentioned processes is that carbon compounds, such as methanol, carbon oxides, carbon disulfide or carbonyl sulfide, are required as raw materials for the preparation of methyl mercaptan. Significant costs are associated with these raw materials and corresponding processes, particularly when the product selectivities for the formation of methyl mercaptan are relatively low. Moreover, complicated purification steps are oftentimes required, whereby a multitude of secondary components cannot be recycled into the process in a cost efficient manner. As a result, selectivity for methyl mercaptan is reduced and the industrial economic viability of the process is diminished.

Processes involving the direct conversion of mixtures obtained from other chemical processes, which comprise methane or higher hydrocarbons, water, hydrogen and optional sulfur-containing compounds, to methyl mercaptan have failed to provide industrially sufficient yields and selectivities in a cost efficient manner, but rather produce a multitude of byproducts including toxic carbon disulfide.

Accordingly, there remains a critical need for a cost efficient process for continuously preparing industrially sufficient yields and selectivities of methyl mercaptan by reacting a reactant mixture comprising solid, liquid and/or gaseous carbon- and/or hydrogen-containing compounds, which may be obtained from other chemical processes, with air or oxygen, and/or water and sulfur.

Based on the relatively low yields and selectivities associated with producing methyl mercaptan according to these conventional processes, as well as the wide spectrum of undesirable and toxic reaction intermediates and byproducts produced from these conventional processes, thereby necessitating employing extensive, time consuming and costly safety measures for protecting manufacturing personnel and the environment, other skilled artisans have failed to discover a solution to this long-felt need.

SUMMARY OF THE INVENTION

The present invention relates to a process for continuously preparing methyl mercaptan by reacting a reactant mixture comprising solid, liquid and/or gaseous carbon- and/or hydrogen-containing compounds with air or oxygen, and/or water and sulfur.

An exemplary aspect of the present invention is to provide a cost efficient process for continuously preparing industrially sufficient yields and selectivities of methyl mercaptan by reacting a reactant mixture comprising solid, liquid and/or gaseous carbon- and/or hydrogen-containing compounds, which may be obtained from other processes, with air or oxygen, and/or water and sulfur.

Another exemplary aspect of the present invention is to provide a more cost efficient process for preparing methyl mercaptan attributable to the utilization of starting materials having significantly lower costs, as compared to the costs associated with the raw materials utilized by the above-mentioned conventional processes.

The foregoing discussion exemplifies certain aspects of the present invention. Additional exemplary aspects of the present invention are discussed in the following detailed description of the invention.

DETAILED DESCRIPTION OF THE INVENTION

Figure 1:
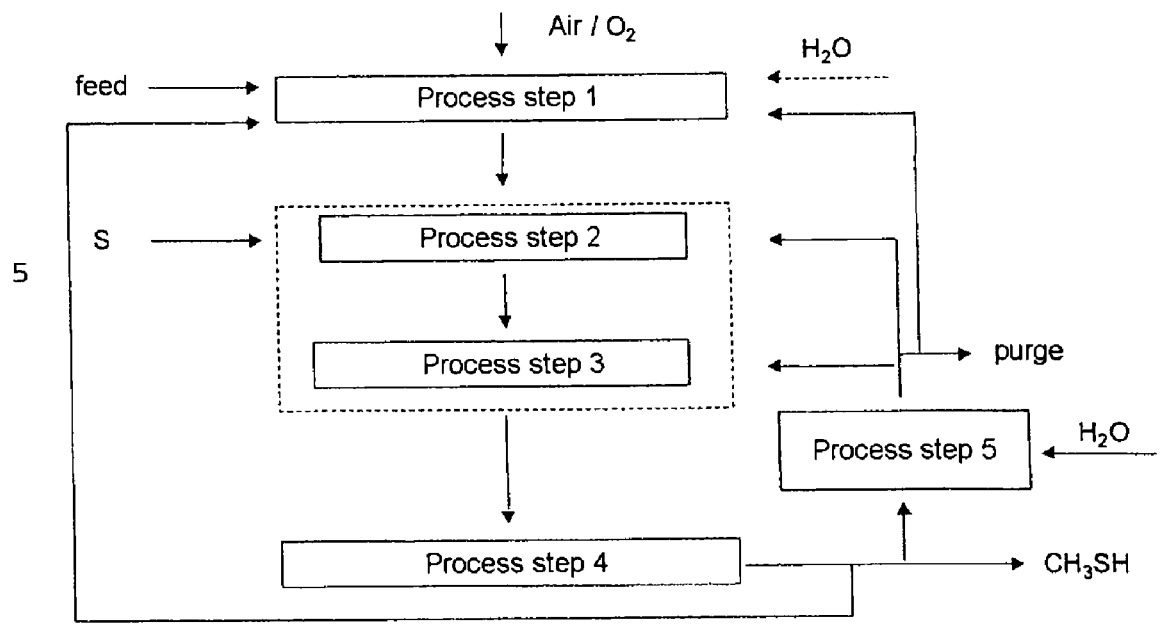
FIG. 1 is a schematic diagram of an exemplary embodiment of the inventive process.

Unless specifically defined, all technical and scientific terms used herein have the same meaning as commonly understood by a skilled artisan in the relevant technological field (e.g., organic chemistry, chemical engineering, etc.).

All processes, materials and examples similar or equivalent to those described herein can used in the practice or testing of the present invention, with suitable processes, materials and examples being described herein. Accordingly, the processes, materials and examples described herein are for illustrative purposes only and are therefore not intended to be limiting, unless otherwise specified.

All patent applications, patent application publications, patents, scientific and technological literature, publications and references specifically mentioned herein are hereby incorporated by reference in their entirety. In case of conflict, the present specification, including definitions set forth herein, are controlling.

Where a closed or open-ended numerical range is described herein, all values and subranges within or encompassed by the numerical range are specifically included as belonging to the original disclosure of the present application as if these values and subranges had been explicitly written out in their entirety.

The present invention relates to a process for continuously preparing methyl mercaptan by reacting a reactant mixture comprising solid, liquid and/or gaseous carbon- and/or hydrogen-containing compounds with air or oxygen, and/or water and sulfur.

The present invention provides a cost efficient process for continuously preparing industrially sufficient yields and selectivities of methyl mercaptan by reacting a reactant mixture comprising solid, liquid and/or gaseous carbon- and/or hydrogen-containing compounds, which may be obtained from other processes, with air or oxygen, and/or water and sulfur.

The present invention also provides a more cost efficient process for preparing methyl mercaptan with higher selectivities due to the utilization of carbon- and hydrogen-containing starting materials, which are obtained from various sources to thereby significantly reduce costs, as compared to the more expensive raw materials utilized by the above-mentioned conventional processes.

Carbon- and hydrogen-containing compounds, including for example hydrocarbons, such as methane, natural gas, heavy oil fractions, residues from crude oil refining, oligomers, polymers and polycyclic aromatics, obtainable as fuel, secondary components and waste streams from various other processes, including energy generation, chemical and biological processes, may be utilized as starting materials, for reaction with air or oxygen, and/or water and sulfur, to thereby significantly reduce costs. For example, selective oxidations form a series of secondary components which additionally contain chemically bound oxygen, including for example alcohols, aldehydes, carboxylic acids and/or carbon oxides. These secondary components are generally incinerated after the removal of the main reaction product or converted in a further chemical reaction to enable the disposal thereof.

Additional sources of reactant mixtures include industrial processes for obtaining organic nitrogen or sulfur compounds, whereby relatively large amounts of byproducts are obtained which generally have to be incinerated or disposed of. For example, the process of the present invention may utilize offgas streams comprising $H_2S$, COS, $SO_2$, $SO_3$-containing compounds, alkyl sulfides or alkyl polysulfides.

Further sources include gases that are obtained from waste streams of power plants for generating energy, manufacturing plants for producing chemical products directly or via separation techniques, or in the course of biological metabolism processes, including for example fermentation and degradation processes. These gases may comprise, as main components, hydrocarbons, carbon oxides, nitrogen compounds, sulfur, organic sulfur compounds, and hydrogen sulfide, as well as other substances, and may be supplied as a reactant mixture to the process of the present invention.

The invention provides a process for continuously preparing methyl mercaptan comprising a first process step of reacting a reactant mixture, which comprises carbon- and hydrogen-containing compounds, air or oxygen, and optionally water and/or sulfur, to produce a gas mixture, which comprises carbon dioxide, carbon monoxide and hydrogen as major components.

The carbon- and/or hydrogen-containing compounds may be provided in the solid, liquid or gaseous state, but are preferably in gaseous form at the time of the reaction.

The reactant mixture may additionally comprise sulfur, for example organic sulfur compounds or hydrogen sulfide.

CO, $CO_2$ and hydrogen are combined in the gas mixture leaving the first process step in a total amount of <100 vol. %, generally 1-90 vol. %, 5-85 vol. %, 10-80 vol. %, 15-75 vol. %, 20-70 vol. %, 25-65 vol. %, 30-60 vol. %, 35-55 vol. % or 40-50 vol. %, and preferably approximately 90 vol. %. CO is preferably present in the gas mixture leaving the first process step in an amount of 1-30 vol. %, 5-25 vol. % or 10-20 vol. %. $CO_2$ is preferably present in the gas mixture leaving the first process step in an amount of 1-55 vol. %, 5-50 vol. %, 10-45 vol. %, 15-40 vol. %, 20-35 vol. % or 25-30 vol. %. Hydrogen is preferably present in the gas mixture leaving the first process step in an amount of 10-90 vol. %, 15-85 vol. %, 20-80 vol. %, 25-75 vol. %, 30-70 vol. %, 35-65 vol. %, 40-60 vol. % or 45-55 vol. %.

The process of the present invention further comprises a second process step of thermally reacting the gas mixture with liquid sulfur and/or gaseous sulfur at a temperature of at least 200° C. and at a pressure of at least 5 bar to produce a gaseous mixture comprising $CO_2/CO/H_2/H_2S$. The gas mixture may be reacted directly without further compression and/or workup. The thermal reaction may be conducted in a single-stage or multistage reaction.

The molar ratio of $CO_2/CO/H_2/H_2S$ is adjusted during the thermal reaction to range from 1:0.1:1:0 to 1:1:10:10, preferably from 1:0.1:4:4 to 1:1:1:1, by feeding in water or hydrogen and optionally hydrogen sulfide, to obtain the gaseous mixture having a molar ratio of $CO_2/CO/H_2/H_2S$ ranging from 1:0.1:1:1 to 1:1:10:10, preferably from 1:0.1:4:4 to 1:1:1:1.

The process of the present invention further comprises a third process step of catalytically converting the gaseous mixture at a temperature of at least 200° C. and at a pressure of at least 5 bar over a catalyst to produce a reaction mixture comprising methyl mercaptan as a primary product.

The process of the present invention further comprises a fourth process step of removing the methyl mercaptan from the reaction mixture.

The process of the present invention may further comprise a fifth process step of recycling a return gas comprising unconverted carbon dioxide ($CO_2$), carbon monoxide (CO), hydrogen ($H_2$) and hydrogen sulfide ($H_2S$) into the process after removing gaseous byproducts and optionally reacting with water. For example, the return gas may be recycled into the third process step of catalytically converting.

The overall selectivity for methyl mercaptan can be increased by recycling carbon-, hydrogen- and/or sulfur-containing compounds into the first, second and/or third process step. Preference is given to recycling carbon- and hydrogen-containing compounds (e.g., hydrocarbons), other sulfur-containing compounds (e.g., polysulfides and carbon disulfide), and byproducts (e.g., water), into the first process step. Preference is given to recycling carbon oxides, hydrogen, carbonyl sulfide and hydrogen sulfide into the second and/or third process step. A particular advantage of the present invention is that polysulfides and toxic carbon disulfide occur with selectivities of less than 1%, and consequently may be recycled into the process without having to be separated and/or disposed of in a technically complicated and costly manner.

As well as methyl mercaptan and water, the gaseous mixture of the third process step comprises unconverted carbon dioxide ($CO_2$), carbon monoxide (CO), hydrogen ($H_2$) and hydrogen sulfide ($H_2S$) starting materials, byproducts, such as carbonyl sulfide, methane, dimethyl sulfide, and small amounts of polysulfides, such as dimethyl disulfide, and toxic carbon disulfide. Unreacted hydrocarbons, as well as gases which are inert in the context of the reaction, for example nitrogen, are also present in the gaseous mixture of the third process step.

The methyl mercaptan thus formed is removed from the gaseous mixture in the fourth process step, for example in several distillation and wash columns at temperatures between 10° C. and 140° C., as described in DE 1768826. Carbon dioxide ($CO_2$), carbon monoxide (CO), hydrogen ($H_2$) and hydrogen sulfide ($H_2S$), byproducts, such as carbonyl sulfide, methane, dimethyl sulfide, and small amounts of polysulfides, such as dimethyl disulfide, and toxic carbon disulfide are recycled into the first, second and/or third process steps.

Advantageously, the return gas of the optional fifth process step is reacted with water, preferably catalytically, in manner such that the return gas primarily comprises carbon dioxide ($CO_2$), carbon monoxide (CO), hydrogen ($H_2$) and hydrogen sulfide ($H_2S$) as main components.

The economic viability of the inventive process is advantageously increased in that complicated and costly removal of potential catalyst poisons, for example sulfur-containing compounds and elemental sulfur, is not needed prior to the metered addition of feedstocks into the first and/or second process steps. Similarly, the removal of such compounds after the reaction in the first process step is likewise unnecessary. These substances can be fed directly into the second process step together with the reaction gases, without further workup and compression thereof, which constitutes a significant cost advantage with regard to the capital and operating costs of the process. Thus, costly desulfurization of the reactant mixture and product gas mixture of the first process step is not required. Advantageously, sulfur or sulfur-containing slags which may be obtained as byproducts of the first process step can be fed directly in solid, liquid or gaseous form as a reactant to the second process step. Gases that are obtained from offgas streams of power plants for generating energy, manufacturing plants for producing chemical products directly or via separation techniques, or those generated during biological processes, including for example degradation or metabolism, can be fed directly into the second process step. These gas mixtures may comprise hydrocarbons, carbon oxides, sulfur and nitrogen compounds as main components in a total concentration of 5-90 vol. % in addition to other substances, and may be fed into the first, second and/or third process steps.

The gas mixture can be converted in the second process stage, optionally with use of a catalyst, by reaction with liquid or gaseous sulfur in a single-stage or multistage process step. In the second process step, full conversion of hydrogen is not attempted. The reaction is performed such that, after the completion of the reaction, the molar ratio of $CO_2/CO/H_2/H_2S$ is from 1:0.1:1:1 to 1:1:10:10, preferably from 1:0.1:4:4 to 1:1:1:1. Advantageously, the gas mixture obtained from the first process step is at a pressure of at least 5 bar and can be fed directly without further compression into the second process step. This constitutes a significant cost advantage, since it is possible to dispense with a compressor stage with high capital and operating costs. The gaseous mixture obtained from the second process step is subsequently fed into the third process step without further compression and workup. An optional apparatus for removing elemental sulfur or sulfur-containing compounds may be connected upstream of this process step. The conversion to methyl mercaptan is effected in the third process step over catalysts.

Advantageous catalysts for utilization in the second and/or third process steps include metal oxide catalysts. Preference is given to catalysts based on alkali metal molybdates and/or alkali metal tungstates, which may be applied to supports, as described in U.S. Pat. No. 5,852,219. Especially suitable are supported catalysts which comprise oxidic molybdenum (Mo) compounds and/or oxidic potassium (K) compounds, where Mo and K may both be present in a single oxidic compound (e.g., $K_2MoO_4$), and/or at least one active oxidic compound of the general formula $A_xO_y$, wherein A is a group 7 element of the periodic table, especially manganese (Mn) or rhenium (Re), and x and y are integers of 1 to 7. Exemplary embodiments of supported catalysts comprising oxidic compounds include $A_xO_y/K_2MoO_4$/support in a weight ratio of (0.001-0.5)/(0.01-0.8)/1, preferably (0.001-0.3)/(0.05-0.5)/1, and $A_xO_y/MoO_3/K_2O$/support in a weight ratio of (0.001-0.5)/(0.01-0.8)/(0.05-0.5)/1, preferably (0.001-0.3)/(0.05-0.3)/(0.03-0.3)/1.

These catalysts preferably comprise one or more promoters selected from oxidic compounds of the general formula $M_xO_y$, wherein M is a transition element or a rare-earth metallic element, and x and y are each an integer of 1 to 7, according to the degree of oxidation of M. M is preferably Mn, Fe, Co, Ni, Sn, La, Ce or Re. Exemplary embodiments of supported catalysts comprising oxidic compounds and promoters include $K_2MoO_4/M_xO_y$/support in a weight ratio of (0.01-0.80)/(0.01-0.1)/1, preferably (0.10-0.60)/(0.01-0.06)/1, and $MoO_3/K_2O/M_xO_y$/support in a weight ratio of (0.10-0.50)/(0.10-0.30)/(0.01-0.1)/1, preferably (0.10-0.30)/(0.10-0.25)/(0.01-0.06)/1.

When any of the aforementioned catalysts are exposed to an atmosphere containing hydrogen sulfide prior to use, the oxidic metal compounds of the catalyst (not to be confused with the oxidic metal compounds of the support material) are converted to sulfidic compounds or mixtures of oxidic and sulfidic compounds which can likewise be used in accordance with the process of the present invention.

Examples of support material include aluminum oxide, silicon dioxide, titanium dioxide, zeolite and activated carbon. When the support is aluminum oxide, the catalyst comprises rhenium oxide and/or rhenium sulfide. A preferred support material is titanium dioxide comprising anatase in an amount of 45-75 mol %, 50-70 mol %, 55-65 mol %, or 60 mol %.

Preparation of an impregnated support is effectuated in a multistage impregnation process, whereby soluble compounds of desired promoters and/or active oxidic compounds are applied to the support. The impregnated support is subsequently dried and optionally calcined.

The second and third process steps are preferably combined into one reaction apparatus, while utilizing identical or different catalysts. Advantageously, bubble columns, reactive distillations, fixed bed reactors, staged reactors or tube bundle reactors may be utilized for the catalyzed conversion to methyl mercaptan.

The reaction in the second process step is carried out at a temperature of at least 200° C., including for example, 200-600° C., 225-550° C., 250-500° C., 275-450° C. and 300-400° C., and at a pressure of at least 1.5 bar, including for example, 1.5-50 bar, 2.0-45 bar, 2.5-40 bar, 3.0-35 bar and 3.5-45 bar. A temperature of 250-500° C. and a pressure of 2.5-40 bar are particularly preferred.

The conversion to methyl mercaptan in the third process step is carried out over catalysts (e.g., catalysts based on alkali metal molybdates and/or alkali metal tungstates) at a temperature of at least 200° C., including for example, 200-600° C., 200-450° C., 225-425° C., 250-400° C., 275-375° C. and 300-350° C., and at a pressure of 1.5-50 bar, 4.0-45 bar, 8-40 bar, 12-35 bar and 16-30 bar. A temperature of 250-400° C. and a pressure of 8-40 bar are particularly preferred.

Advantageous catalysts that may be utilized in the second and/or third process step include for example, those described in WO 2005/040082, WO 2005/021491, WO 2006/015668 and WO 2006/063669.

In a further embodiment of the invention, the second and third process step are combined in one apparatus.

The product gas mixtures can be separated by various processes, including for example, the separation process described in EP 0850923 and U.S. Pat. No. 5,866,721.

Unconverted carbon oxides, hydrogen and hydrogen sulfide, gaseous byproducts (e.g., carbonyl sulfide), and hydrocarbons may be recycled into the process at the first, second and/or third process stage via addition to a reactant stream, for example. Advantageously, before recycling into the second and/or third process stage, the molar ratio of $CO_2CO/H_2/H_2S$ is adjusted from 1:0.1:1:1 to 1:1:10:10 by reaction with water, which may be accomplished with or without catalysis in a fixed bed reactor, a reaction tube, a wash column or a reactive distillation at a temperature of at least 120° C. Advantageously, secondary components, for example carbonyl sulfide and carbon disulfide, are hydrolyzed in this process step to carbon dioxide and hydrogen sulfide, which re-entered into the second and/or third process step as reactants. Sulfides, polysulfides and hydrocarbons, which are obtained during the removal of methyl mercaptan in the fourth process step, can be recycled without further workup into the first and/or second process step, thereby increasing the overall selectivity of the process for methyl mercaptan, based on carbon, to 80-95% or more.

FIG. 1 is a schematic diagram of an exemplary embodiment of the inventive process. An advantageous economic aspect of the inventive process in the ability to utilize a multitude of solid, liquid and/or gaseous carbon- and hydrogen-containing starting materials, which are metered into the first process step, and the fact that this reactant stream need not be purified and desulfurized in a complicated, time consuming and costly manner. Moreover, some if not all of the byproducts that are removed in the fourth process step may be recycled into the first, second and/or third process step. Advantageously, all process steps may optionally be carried out under the same operating conditions (e.g., the same pressure range), thereby making it possible to dispense with costly compression of the gases between individual process steps. The reactions are effected at the starting pressure of the gases which leave the first process step or are metered into the second and/or third process step from other sources under pressure. Advantageously, this pressure is adjusted to 1.5-50 bar, 4.0-45 bar, 8-40 bar, 12-35 bar and 16-30 bar, with a pressure of 8-40 bar being particularly preferred. Gases which are inert in the context of the process are discharged from the process continuously or discontinuously via a purge gas stream.

The above written description is provided to thereby enable a skilled artisan to practice the invention described and claimed herein. Various modifications to the exemplary aspects will be readily apparent to those skilled in the art, and general principles and features defined herein may be applied to other non-exemplified aspects without departing from the spirit and scope of the present invention. Thus, the present invention is not intended to be limited to the aspects exemplified herein, but is to be accorded the broadest reasonable scope consistent with the general principles and features disclosed herein.

Having generally described the present invention, a further understanding can be obtained by reference to specific examples, which are provided herein merely for purposes of illustration only, and are not intended to be limiting unless otherwise specified.

EXAMPLE 1

Steam reformation of a hydrocarbon feed gas stream and subsequent reaction with sulfur afforded a gas mixture which comprises the main components $CO_2/CO/H_2/H_2S$ in a molar ratio of about 1/0.1/4/4. At a reaction temperature of 250-350° C. and a pressure of 30 bar, the reactants were converted in the third process step over various catalysts. The catalytic activity was initially determined for a single pass through the reactor.

TABLE 1

| Catalyst | Conversion $(CO_2)$/% | Selectivity (MC)/% | Selectivity (CO)/% | Selectivity $(CH_4)$/% |
| --- | --- | --- | --- | --- |
| Catalyst A $Re_2O_7/K_2MoO_4/TiO_2$ | 55.8 | 82.2 | 11.8 | 4.5 |
| Catalyst B $SnO_2/Re_2O_7/K_2MoO_4/TiO_2$ | 53.5 | 82.6 | 9.9 | 4.8 |
| Catalyst C $Mn_xO_y/K_2MoO_4/TiO_2$ | 50.1 | 81.5 | 12.6 | 3.5 |

MC = methyl mercaptan

EXAMPLE 2

Methyl mercaptan was removed from the product gas stream in the fourth process step 4 of Example 1. The return gas comprising the main components $CO_2$, $H_2$, CO and $H_2S$ was, after reaction with water in the fifth process step, recycled into the third process step and converted under analogous reaction conditions to those described in Example 1. Over catalysts A-C, methyl mercaptan selectivities of 90-94% were remarkably achieved.

Numerous modifications and variations on the present invention are obviously possible in light of the above disclosure and thus the present invention may be practiced otherwise than as specifically described herein without departing from sprit and scope of the present invention. Accordingly, it is therefore to be understood that the foregoing disclosure is merely illustrative of exemplary aspects of the present inven-

The invention claimed is:

1. A process for continuously preparing methyl mercaptan, comprising:
   (I) reacting a reactant mixture comprising
      at least one carbon- and hydrogen-containing compound,
      air or oxygen, and
      optionally, water,
      to produce a gas mixture comprising carbon dioxide ($CO_2$), carbon monoxide (CO), hydrogen ($H_2$) at least one gas obtained from at least one offgas stream streams of a process for oxidation of at least one hydrocarbon and/or for synthesis of at least one nitrogen- and/or sulfur-containing compound, and, optionally, hydrogen sulfide ($H_2S$);
   (II) thermally reacting said gas mixture with liquid sulfur and/or gaseous sulfur in a single-stage or multistage reaction at a temperature of at least 200° C. and at a pressure of at least 5 bar to produce a gaseous mixture comprising $CO_2$, CO, $H_2$, and $H_2S$,
      wherein a molar ratio of $CO_2/CO/H_2/H_2S$ is adjusted during said thermally reacting to range from 1:0.1:1:0 to 1:1:10:10 by feeding in water or hydrogen and optionally hydrogen sulfide, to obtain said gaseous mixture having a molar ratio of $CO_2/CO/H_2/H_2S$ ranging from 1:0.1:1:1 to 1:1:10:10;
   (III) catalytically converting said gaseous mixture at a temperature of at least 200° C., at a pressure of at least 5 bar, and over a catalyst, to produce a reaction mixture comprising methyl mercaptan;
   (IV) removing said methyl mercaptan from said reaction mixture to produce a return gas; and
   (V) optionally, recycling said return gas comprising unconverted $CO_2$, CO, $H_2$ and $H_2S$ into the process after removing gaseous byproducts and, optionally, reacting with water,
   wherein said gas mixture is directly fed from said reacting (I) to said thermally reacting (II) at a pressure of at least 5 bar, without further compression, said gaseous mixture is directly fed from said thermally reacting (II) to said catalytically converting (III) at a pressure of at least 5 bar, and said reaction mixture is directly fed from said catalytically converting (III) to said removing (IV) at a pressure of at least 5 bar.

2. The process according to claim 1, wherein said reactant mixture further comprises water.

3. The process according to claim 1, wherein said reactant mixture further comprises at least one nitrogen-containing compound.

4. The process according to claim 1, wherein said reactant mixture further comprises at least one sulfur-containing compound.

5. The process according to claim 1, wherein said reactant mixture further comprises at least one compound selected from the group consisting of a carbon-containing compound, a hydrogen-containing compound, and an oxygen-containing compound.

6. The process according to claim 1, wherein said reactant mixture further comprises at least one compound selected from the group consisting of a carbon-containing compound, a hydrogen-containing compound, and an oxygen-containing compound, which are converted by partial oxidation with air or oxygen, or by steam reformation, to produce said gas mixture comprising $CO_2$, CO, $H_2$ and, optionally, $H_2S$.

7. The process according to claim 1, wherein said at least one carbon- and hydrogen-containing compound is converted by partial oxidation with air or oxygen, or by steam reformation, to produce said gas mixture comprising $CO_2$, CO, $H_2$, and, optionally, $H_2S$.

8. The process according to claim 1, wherein a whole or a part of said reactant mixture is at least one gas obtained from at least one offgas stream of a process for generating energy and/or producing a chemical product.

9. The process according to claim 1, wherein at least one gas generated in a biological metabolism process is introduced into said thermally reacting (II) and/or said catalytically converting (III).

10. The process according to claim 1, wherein at least one gas comprising at least one compound selected from the group consisting of methane, a higher hydrocarbon having a $C_2$-$C_6$ radical, $CO_2$, and CO are supplied to the process as a raw material.

11. The process according to claim 1, wherein said thermally reacting (II) to produce said gaseous mixture comprising $CO_2$, CO, $H_2$, and $H_2S$, is carried out in the presence of liquid sulfur and/or gaseous sulfur in a single-stage or multi-stage reaction that is optionally catalyzed or uncatalyzed.

12. The process according to claim 1, wherein a molar ratio of $CO_2/CO/H_2/H_2S$ at the end of said thermally reacting (II) ranges from 1:0.1:4:4 to 1:1:1:1.

13. The process according to claim 1, wherein said return gas comprising unconverted $CO_2$, CO, $H_2$, and $H_2S$, is recycled into said reacting (I), said thermally reacting (II), and/or said catalytically converting (III).

14. The process according to claim 1, wherein at least one carbon-, hydrogen-, and sulfur-containing gaseous byproduct is recycled into said reacting (I), said thermally reacting (II), and/or said catalytically converting (III).

15. The process according to claim 1, wherein a total amount of $H_2S$ present in said catalytically converting (III) is established by varying a ratio of carbon to hydrogen present in said reactant mixture, by varying a content of $H_2$ present in said gas mixture which is fed into said thermally reacting (II), and/or by varying at least one process parameter selected from the group consisting of residence time, reaction temperature, and reaction pressure.

16. The process according to claim 1, wherein at least one reactive distillation, bubble column reactor, fixed bed reactor, staged reactor, or tube bundle reactor is utilized in said thermally reacting (II) and/or said catalytically converting (III).

17. The process according to claim 1, wherein said thermally reacting (II) and said catalytically converting (III) are combined into one reaction apparatus.

18. The process according to claim 1, wherein a sulfur-containing compound is not removed after said reacting (I) and said thermally reacting (II).

19. The process according to claim 1, wherein overall selectivity for carbon disulfide and polysulfides is less than 1%.

20. The process according to claim 1, wherein the catalyst is selected from the group consisting of an alkali metal tungstate, a halide-containing alkali metal tungstate, alkali metal molybdate, and a halide-containing alkali metal molybdate, and
   wherein the catalyst comprises at least one promoter selected from the group consisting of a transition metal oxide, and a transition metal sulfide.

21. The process according to claim 1, wherein said gaseous mixture is converted in said catalytically converting (III) over the catalyst, which is at least one selected from the group consisting of a molybdate-containing catalyst and a tungstate-containing catalyst, and wherein the catalyst comprises at least one promoter selected from the group consisting of an alkali metal oxide, an alkali metal sulfide, a transition metal oxide, and a transition metal sulfide.

22. The process according to claim 1, wherein at least one catalyst is selected from the group consisting of an alkali metal tungstate, a halide-containing alkali metal tungstate, alkali metal molybdate, and a halide-containing alkali metal molybdate, and wherein the at least one catalyst comprises at least one promoter selected from the group consisting of a cobalt oxide, cobalt sulfide, manganese oxide, manganese sulfide, rhenium oxide, and a rhenium sulfide.

23. The process according to claim 1, wherein the catalyst is at least one supported catalyst selected from the group consisting of an oxidic molybdenum (Mo) compound and an oxidic potassium (K) compound, wherein Mo and K may both be present in a single oxidic compound, and wherein the at least one supported catalyst comprises at least one active oxidic compound of formula $A_xO_y$, wherein A is a group 7 element of the periodic table, and x and y are each individually an integer of 1 to 7.

24. The process according to claim 23, wherein A is manganese (Mn) or rhenium (Re).

25. The process according to claim 23, wherein the at least one supported catalyst is selected from $A_xO_y/K_2MoO_4$/support in a weight ratio of (0.001-0.5)/(0.01-0.8)/1, and $A_xO_y$/$MoO_3/K_2O$/support in a weight ratio of (0.0001-0.5)/(0.01-0.8)/(0.005-0.5)/1.

26. The process according to claim 23, wherein the at least one supported catalyst is selected from $A_xO_y/K_2MoO_4$/support in a weight ratio of (0.001-0.3)/(0.05-0.5)/1, and $A_xO_y$/$MoO_3/K_2O$/support in a weight ratio of (0.001-0.3)/(0.05-0.3)/(0.03-0.3)/1.

27. The process according to claim 23, wherein the at least one supported catalyst comprises at least one promoter, which is an oxidic compound of formula $M_xO_y$, and wherein M is a transition element or a rare-earth metallic element, and x and y are each individually an integer of 1 to 7.

28. The process according to claim 27, wherein the at least one promoter is selected from $K_2MoO_4/M_xO_y$/support in a weight ratio of (0.01-0.80)/(0.01-0.1)/1, and $MoO_3/K_2O/M_xO_y$/support in a weight ratio of (0.10-0.50)/(0.10-0.30)/(0.01-0.1)/1.

29. The process according to claim 27, wherein the at least one promoter is selected from $K_2MoO_4/M_xO_y$/support in a weight ratio of (0.10-0.60)/(0.01-0.06)/1, and $MoO_3/K_2O/M_xO_y$/support in a weight ratio of (0.10-0.30)/(0.10-0.25)/(0.01-0.06)/1.

30. The process according to claim 1, wherein the catalyst is exposed to an $H_2S$-containing atmosphere prior to use.

31. The process according to claim 1, wherein a catalyst selected from the group consisting of an alkali metal tungstate, a halide-containing alkali metal tungstate, an alkali metal molybdate, and a halide-containing alkali metal molybdate, is utilized in said thermally reacting (II), and wherein the catalyst utilized in said thermally reacting (II) comprises at least one promoter selected from the group consisting of a transition metal oxide and a transition metal sulfide.

32. The process according to claim 1, wherein said gas mixture is reacted in said thermally reacting (II) over a catalyst is at least one selected from the group consisting of a molybdate-containing catalyst, and a tungstate-containing catalyst, and wherein the catalyst utilized in said thermally reacting (II) comprises at least one promoter selected from the group consisting of an alkali metal oxide, an alkali metal sulfide, a transition metal oxide, and a transition metal sulfide.

33. The process according to claim 1, wherein at least one catalyst selected from the group consisting of an alkali metal tungstate, a halide-containing alkali metal tungstate, an alkali metal molybdate, and a halide-containing alkali metal molybdate, is utilized in said thermally reacting (II), and wherein the at least one catalyst utilized in said thermally reacting (II) comprises at least one promoter selected from the group consisting of a cobalt oxide, a cobalt sulfide, a manganese oxide, a manganese sulfide, a rhenium oxides, and a rhenium sulfide.

34. The process according to claim 1, wherein at least one supported catalyst selected from the group consisting of an oxidic molybdenum (Mo) compound and an oxidic potassium (K) compound, wherein Mo and K may both be present in a single oxidic compound, is utilized in said thermally reacting (II), and wherein the at least one supported catalyst utilized in said thermally reacting (II) comprise at least one active oxidic compound of formula $A_xO_y$, wherein A is a group 7 element of the periodic table, and x and y are each individually an integer of 1 to 7.

35. The process according to claim 34, wherein A is manganese (Mn) or rhenium (Re).

36. The process according to claim 34, wherein the at least one supported catalyst utilized in said thermally reacting (II) is selected from $A_xO_y/K_2MoO_4$/support in a weight ratio of (0.001-0.5)/(0.01-0.8)/1, and $A_xO_y/MoO_3/K_2O$/support in a weight ratio of (0.0001-0.5)/(0.01-0.8)/(0.005-0.5)/1.

37. The process according to claim 34, wherein the at least one supported catalyst utilized in said thermally reacting (II) is selected from $A_xO_y/K_2MoO_4$/support in a weight ratio of (0.001-0.3)/(0.05-0.5)/1, and $A_xO_y/MoO_3/K_2O$/support in a weight ratio of (0.001-0.3)/(0.05-0.3)/(0.03-0.3)/1.

38. The process according to claim 34, wherein the at least one supported catalyst utilized in said thermally reacting (II) comprises at least one promoter, which is an oxidic compound of formula $M_xO_y$, and wherein M is a transition element or a rare-earth metallic element, and x and y are each individually an integer of 1 to 7.

39. The process according to claim 38, wherein the at least one promoter is selected from the group consisting of $K_2MoO_4/M_xO_y$/support in a weight ratio of (0.01-0.80)/(0.01-0.1)/1, and $MoO_3/K_2O/M_xO_y$/support in a weight ratio of (0.10-0.50)/(0.10-0.30)/(0.01-0.1)/1.

40. The process according to claim 38, wherein the at least one promoter is selected from the group consisting of $K_2MoO_4/M_xO_y$/support in a weight ratio of (0.10-0.60)/(0.01-0.06)/1, and $MoO_3/K_2O/M_xO_y$/support in a weight ratio of (0.10-0.30)/(0.10-0.25)/(0.01-0.06)/1.

41. The process according to claim 1, wherein a catalyst utilized in said thermally reacting (II) is exposed to an $H_2S$-containing atmosphere prior to use.

* * * * *